(12) United States Patent
Yoshisato

(10) Patent No.: US 6,534,670 B2
(45) Date of Patent: Mar. 18, 2003

(54) CATALYST AND PROCESS FOR THE PREPARATION OF AROMATIC CARBONATES

(75) Inventor: Eishin Yoshisato, Yamaguchi (JP)

(73) Assignee: Teijin Limited, Osaka (JP)

( * ) Notice: Subject to any disclaimer, the term of this patent is extended or adjusted under 35 U.S.C. 154(b) by 0 days.

(21) Appl. No.: 09/485,093

(22) PCT Filed: Aug. 4, 1998

(86) PCT No.: PCT/JP98/03473

§ 371 (c)(1),
(2), (4) Date: Feb. 4, 2000

(87) PCT Pub. No.: WO99/06142

PCT Pub. Date: Feb. 11, 1999

(65) Prior Publication Data

US 2002/0198397 A1 Dec. 26, 2002

(30) Foreign Application Priority Data

Aug. 4, 1997 (JP) .............................................. 9-209059
Feb. 6, 1998 (JP) ............................................ 10-025700
May 11, 1998 (JP) ........................................... 10-127497

(51) Int. Cl.$^7$ ........................... C07C 69/96; B01J 23/44
(52) U.S. Cl. ...................................... 558/274; 502/302
(58) Field of Search ........................... 502/302; 558/274

(56) References Cited

U.S. PATENT DOCUMENTS 4,134,852 A * 1/1979 Volin ..................... 502/302 X
5,789,339 A * 8/1998 Ziebarth et al. ............ 502/525
6,001,768 A * 12/1999 Buysch et al. .............. 502/230

FOREIGN PATENT DOCUMENTS

| EP | 0736324 | * 3/1996 |
|---|---|---|
| JP | 81038144 | 9/1981 |
| JP | 81038145 | 9/1981 |
| JP | 62-269747 | 11/1987 |
| JP | 1165551 | 6/1989 |
| JP | 5058961 | 3/1993 |
| JP | 5-220395 | 8/1993 |
| JP | 6009505 | 1/1994 |
| JP | 6041020 | 2/1994 |
| JP | 6172268 | 6/1994 |
| JP | 6172269 | 6/1994 |
| JP | 7010812 | 1/1995 |
| JP | 7145107 | 6/1995 |
| JP | 8092168 | 4/1996 |
| JP | 80999935 | 4/1996 |
| JP | 8-281108 | 10/1996 |
| JP | 8281114 | 10/1996 |
| JP | 9-56928 | 3/1997 |
| JP | 8283206 | 9/1997 |
| JP | 01-304048 | * 12/1998 |

OTHER PUBLICATIONS

Tanaka, H. et al. Perovskite–Pd Three–Way Catalysts for Automotive Applications. Soc. Automot. Eng. SP–968 (Catalyst and Emission Control Technology) 1993, pp. 63–76.*

* cited by examiner

Primary Examiner—Joseph K. McKane
Assistant Examiner—Kamal Saeed
(74) Attorney, Agent, or Firm—Sughrue Mion, PLLC

(57) ABSTRACT

Aromatic carbonates can be prepared economically and efficiently by reacting an aromatic hydroxy compound with carbon monoxide and oxygen in the presence of a catalyst wherein a palladium compound is supported on a perovskite-type composite oxide represented by the following formula (1) or (1'):

$$M_{(1-x)}M'_xM''O_y \qquad (1)$$

(wherein, M is a group IIIB metal; x is a number of 0 to 1; M' is a metal having an ionic radius of 0.90 Å or more; M" is Mn, Cr, Co, Fe, Ni or Cu; y is a number of 2.5 to 3.5), or $$L_{(1-x)}L'_xL''O_y \qquad (1')$$

(wherein, L is a group IIA or IVA metal taking a divalent state in the form of an oxide; x is a number of 0 to 1; L' is a metal having an ionic radius of 0.90 Å or more; L" is a group IVA, IVB or IIIB metal taking a tetravalent state in the form of an oxide; y is a number of 2.5 to 3.5), and the palladium accounts for 0.01 to 15% of the catalyst by weight.

10 Claims, 10 Drawing Sheets

CATALYST AND PROCESS FOR THE PREPARATION OF AROMATIC CARBONATES

This application is a 371 of PCT/JP98/03473 filed Aug. 4, 1998.

TECHNICAL FIELD

The present invention relates to catalysts for the synthetic reaction of an aromatic carbonate and a process for the preparation of aromatic carbonates by reacting an aromatic hydroxy compound with carbon monoxide and oxygen in the presence of said catalyst.

BACKGROUND ART

The aromatic carbonate represented by diphenyl carbonate is a useful compound as the raw material for polycarbonate, or the like. As a process for preparing an aromatic carbonate, the process in which an aromatic hydroxy compound is made to react with phosgene has been conventionally used. However, this process has many troubles as an industrial production method since phosgene is strongly toxic, and further the process produces a large amount of byproducts consisting of inorganic salts. In these circumstances, several methods which produce aromatic carbonates without using phosgene have been proposed.

For example, JP-B 56-38144 (JP-B means Japanese examined patent publication) describes a method in which phenol is made to react with carbon monoxide by using a compound containing a metal of the groups of IIIA, IVA, VA, VIA, IB, IIB, IVB, VB, VIB, VIIB and VIIIB in the periodic table and a base in the presence of a palladium catalyst. Further, JP-B 56-38145 discloses a method using a palladium compound, a manganese complex or a cobalt complex, a base, and a drying agent; JP-A 1-165551 (JP-A means Japanese unexamined patent publication) discloses a method using a palladium compound, an iodine compound and zeolite; JP-A 2-104565 discloses a method using a palladium compound, a manganese compound, a tetraalkylammonium salt and a quinone; JP-A 558961 discloses a method using a mixture consisting of a palladium compound, an inorganic compound selected from cobalt, iron, cerium, manganese, molybdenum, samarium, vanadium, chromium and copper, a promotor selected from an aromatic ketone, an aliphatic ketone and an aromatic polycyclic coal tar hydrocarbon, and a quaternary ammonium salt; JP-A 6-9505 discloses a method using a palladium compound, a cerium compound, a quaternary ammonium salt, etc.; JP-A 6-41020 discloses a method using a palladium compound, an inorganic promotor selected from manganese, cobalt and copper, and a nitrile compound; JP-A 6-172268 discloses a method using a palladium compound, a penta coordinated complex of cobalt, a quaternary ammonium salt, etc.; JP-A 6-172269 discloses a method using a palladium compound, an inorganic promotor selected from cobalt, manganese and copper, and an organic cocatalyst such as a quaternary ammonium salt or terpyridine; JP-A 7-10812 discloses a method using a palladium compound, cerium compound and an alkali metal halide; JP-A 7-145107 discloses a method using a palladium compound, a manganese compound and an alkali metal halide; JP-A 8-92168 discloses a method using a palladium compound, an alkali metal halide and an activated carbon; JP-A 8-99935 discloses a method using a palladium compound, a lead compound, a quaternary ammonium halide salt and a copper compound; JP-A 8-281108 discloses a method performing the reaction using a catalyst consisting of a platinum group metal compound carried on a support containing an oxide of a metal of Ti, V, Mn, Cr, Fe, Co, Ni, Cu, La, Nb, Mo or Pb, a rare earth metal or an actinide in the presence of a cocatalyst such as a manganese salt or a cobalt salt, a quaternary ammonium or phosphonium salt, and a base; JP-A 8-281114 discloses a method performing the reaction using a supported catalyst carrying a platinum group metal compound and a metal compound acting as a cocatalyst on a known support in the presence of a quaternary ammonium or phosphonium salt, and a base; and JP-A 8-283206 discloses a method using a platinum group metal compound, a cocatalyst such as a manganese salt or a cobalt salt, a quaternary salt and, a base, and further additionally using an inhomogeneous promotor such as a metal oxide, a carbide, a nitride or a boride, and so forth.

As mentioned above, for a conventional catalyst system which produces an aromatic carbonate by reacting an aromatic hydroxy compound redox agent such as a manganese, cobalt or cerium metal compound in the presence of a promotor such as a quaternary ammonium salt, and further an expensive additive such as a base, a ligand, hydroquinone or quinone is used. Therefore, this not only makes the reaction system complicated and the separation of the aromatic carbonate of the reaction product from the catalyst components difficult, but also the selectivity of the reaction is not always sufficiently high, and the purification is also difficult. In addition, the yield is insufficient, and in order to increase the reaction rate, the total pressure is kept at relatively high level. An explosive mixed gas being possibly formed during operation, it is necessary to pay sufficient care on its composition, and thus the conventional method has safety problems.

Problems to be Solved by the Invention

Heretofore, a supported catalyst enabling the economical efficient production of an aromatic carbonate by reacting an aromatic hydroxy compound with carbon monoxide and oxygen therefore has not been found. The object of the present invention is to find a supported catalyst capable of exhibiting high activity and selectivity which enables the economical efficient production of an aromatic carbonate by reacting an aromatic hydroxy compound with carbon monoxide and oxygen, and a method for producing the aromatic carbonate by using the catalyst.

DISCLOSURE OF THE INVENTION

The inventors of the present invention had pursued studies zealously to find the component of a support having said functions, and they noticed a perovskite-type composite oxide, found a composition extremely effective as the component of support of the present invention out of compositions of perovskite-type composite oxide and completed the present invention.

That is, the present invention proposes a catalyst for the synthetic reaction of an aromatic carbonate carrying a palladium metal or compound ion a perovskite-type composite oxide represented by the following formula (1) or (1').

$$M_{(1-x)}M'_xM''O_y \quad (1)$$

(wherein, M is a group IIIB metal; x is a number of 0 to 1; M' is a metal having an ionic radius of 0.90 Å or more; M" is Mn, Cr, Co, Fe, Ni or Cu; y is a number of 2.5 to 3.5), or $$L_{(1-x)}L'_xL''O_y \quad (1')$$

(wherein, L is a group IIA or IVA metal taking a divalent state in the form of an oxide; x is a number of 0 to 1; L' is a metal having an ionic radius of 0.90 Å or more; L" is a group IVA, IVB or IIIB metal taking a tetravalent state in the form of an oxide; y is a number of 2.5 to 3.5), and a method which produces the objective aromatic carbonate in high yield and high selectivity, and in an economical manner by reacting an aromatic hydroxy compound with carbon monoxide and oxygen using said catalyst in the presence of a quaternary ammonium or phosphonium salt and a redox agent.

Explanation of the marks.
1. Reaction gas.
2. Reaction gas.
3. Valve.
4. Valve.
5. Pressure controller.
6. Pressure controller.
7. Constant flow gas feeding apparatus (mass flow controller).
8. Constant flow gas feeding apparatus (mass flow controller).
9. Gas mixing and preheating device.
10. Reactor.
11. Cold trap.
12. Pressure controller.

Figure 2:
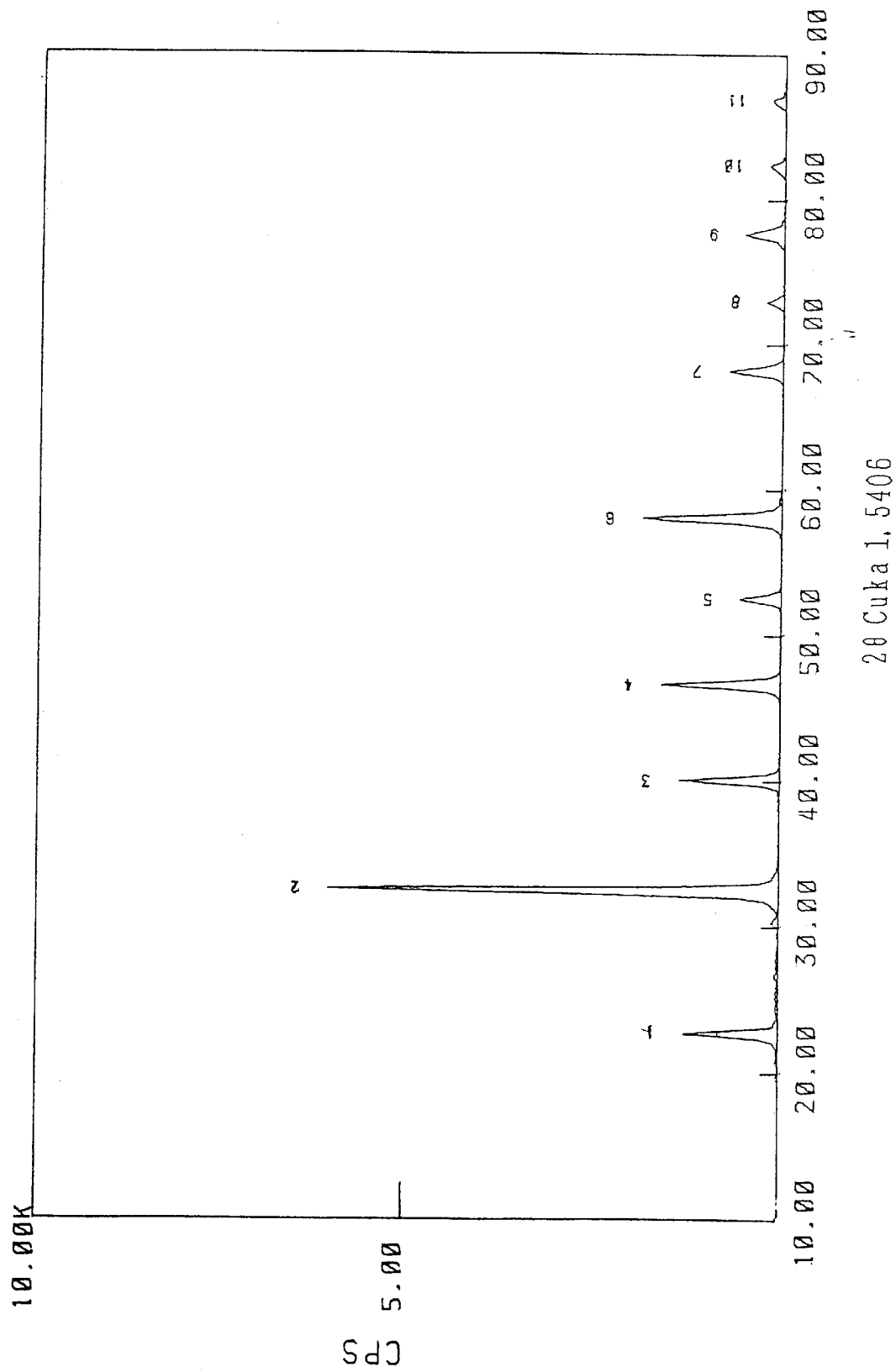

FIG. 2 is an X-ray diffraction chart of $La_{0.5}Pb_{0.5}MnO_3$ (Example 1).

Figure 3:
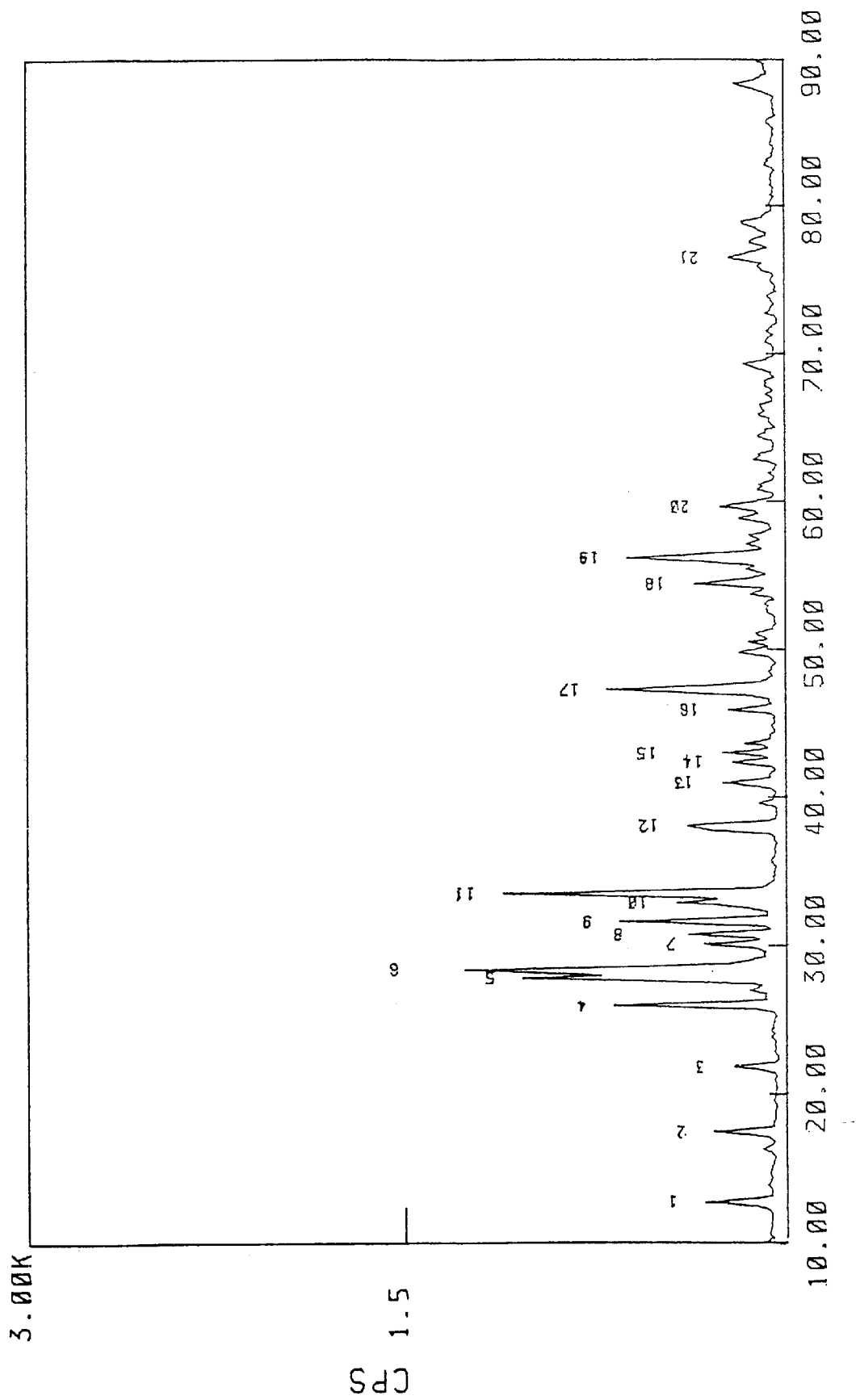

FIG. 3 is an X-ray diffraction chart of $Ce_{0.5}Pb_{0.5}MnO_3$ (Example 2).

Figure 4:
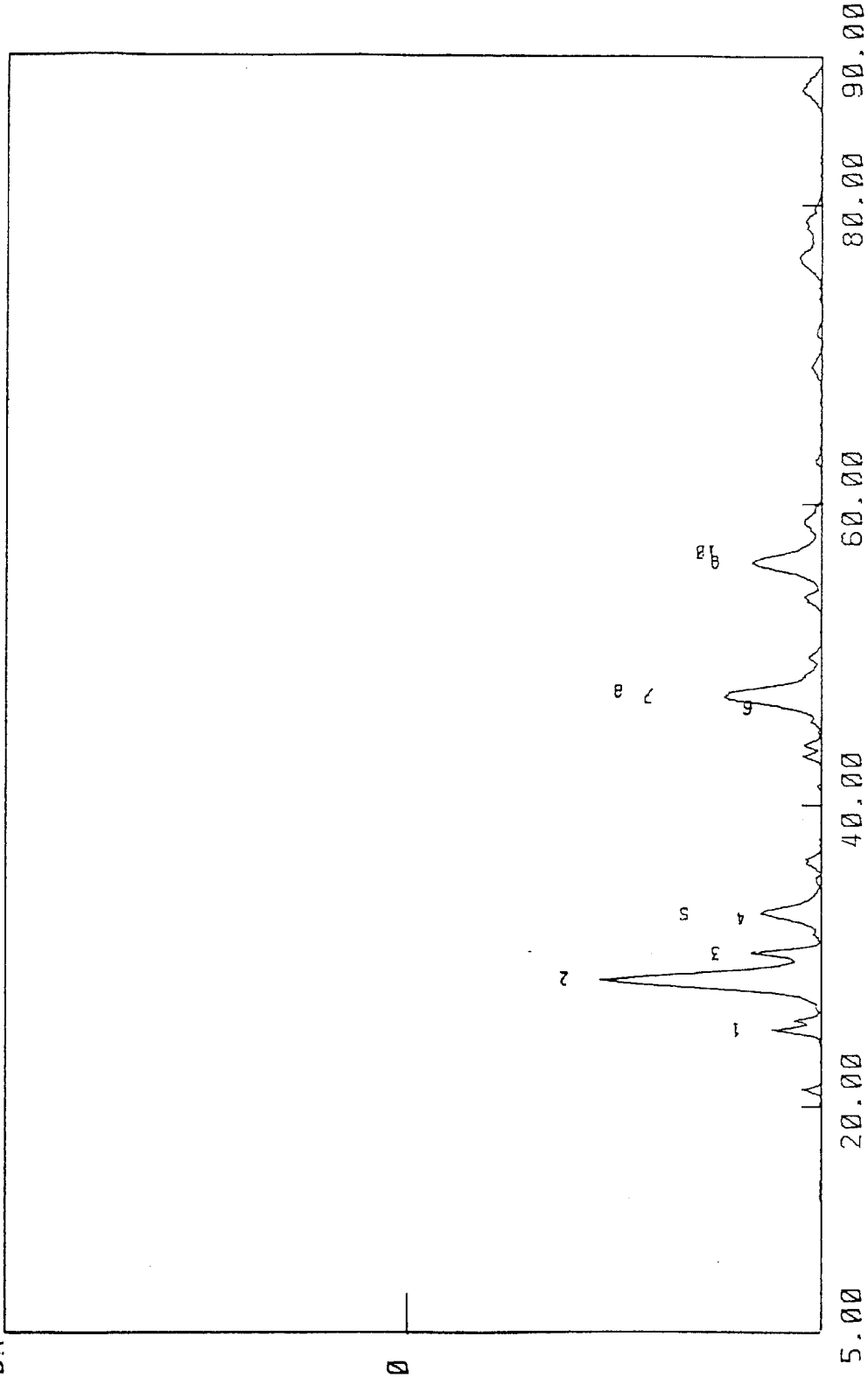

FIG. 4 is an X-ray diffraction chart of $Sr_{0.6}Pb_{0.4}CeO_3$ (Example 3).

Figure 5:
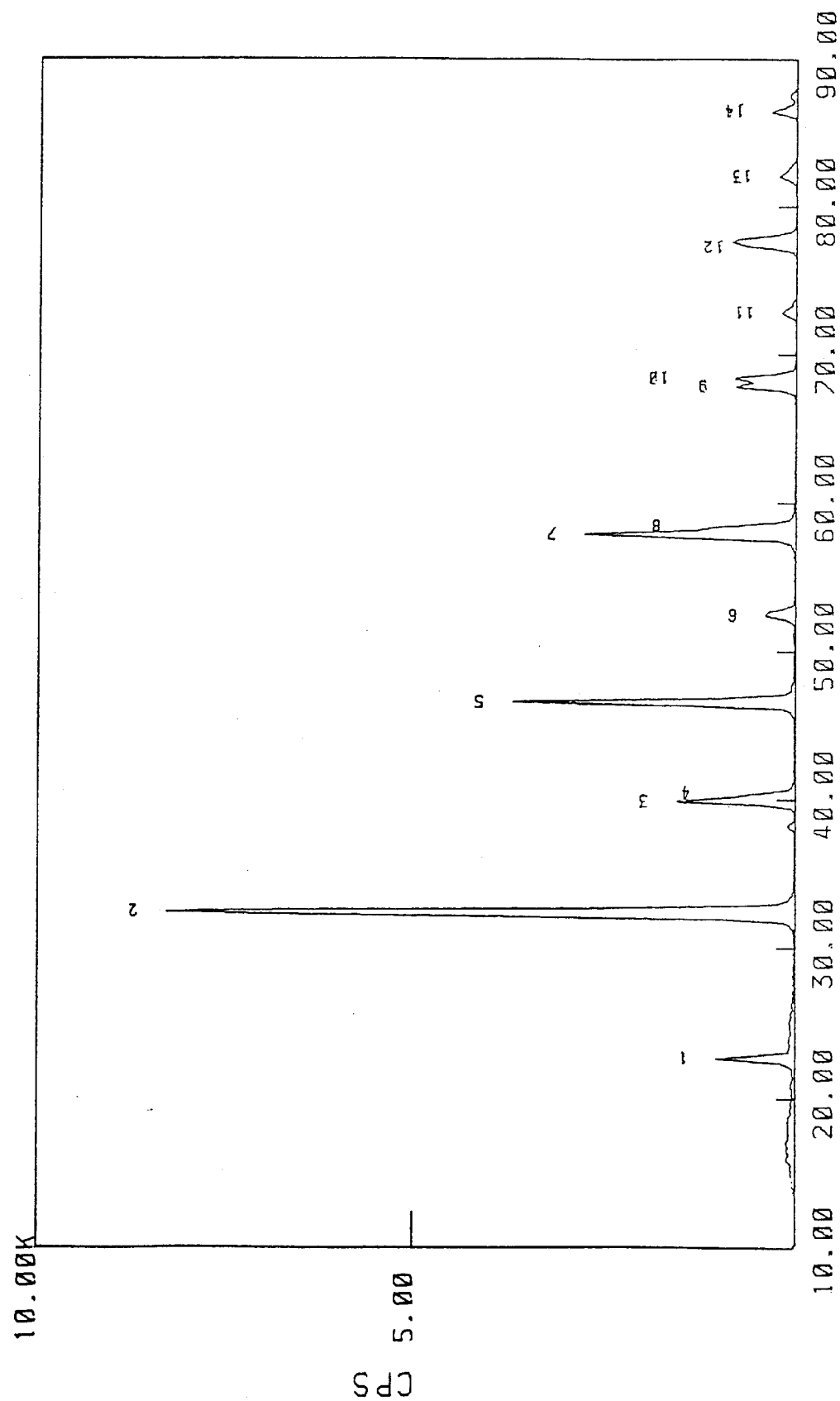

FIG. 5 is an X-ray diffraction chart of $La_{0.8}Sr_{0.2}MnO_3$ (Example 4).

Figure 6:
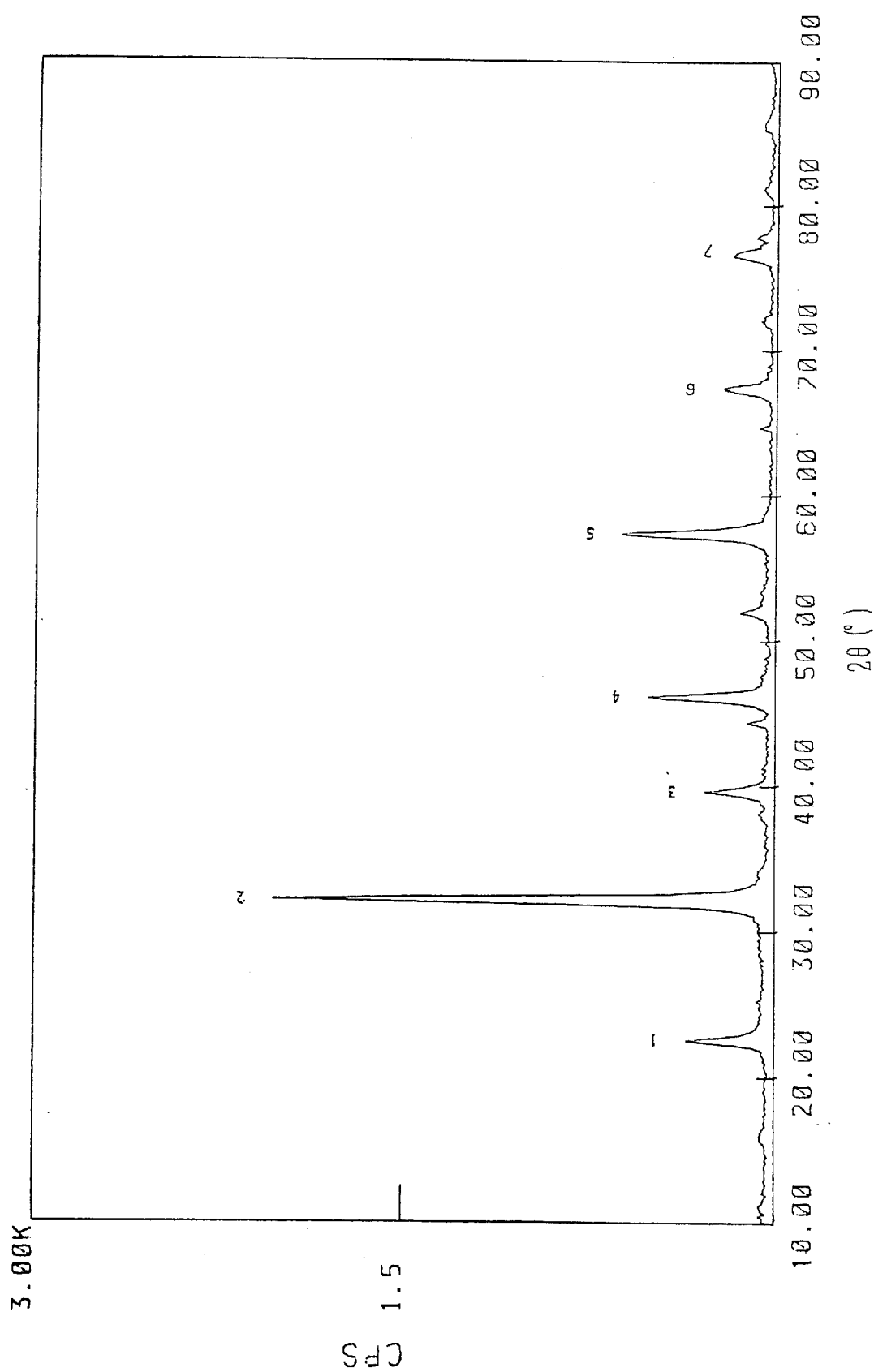

FIG. 6 is an X-ray diffraction chart of $La_{0.6}Pb_{0.4}CUO_3$ (Example 7).

Figure 7:
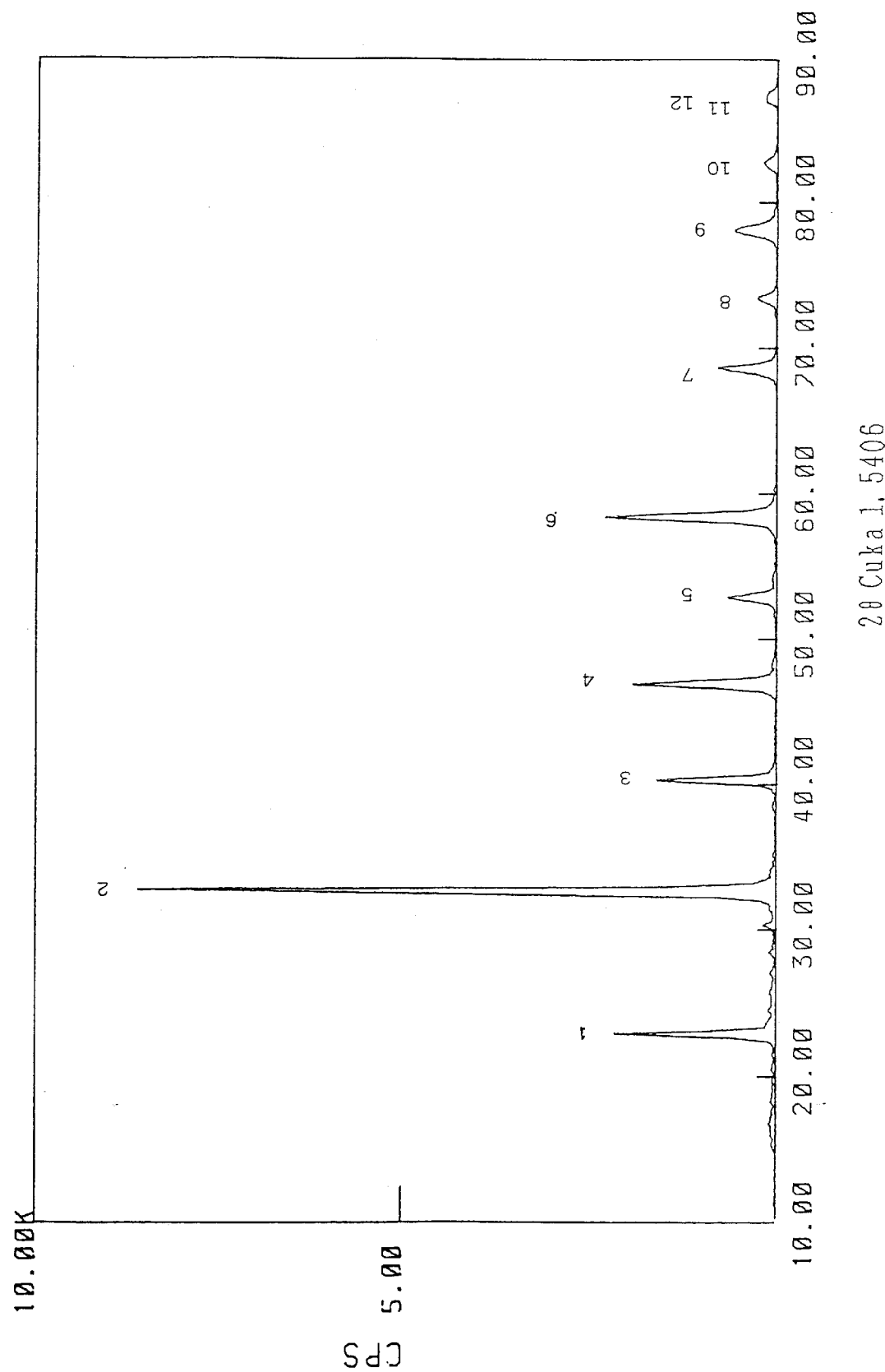

FIG. 7 is an X-ray diffraction chart of $Nd_{0.6}Pb_{0.4}MnO_3$ (Example 10).

Figure 8:
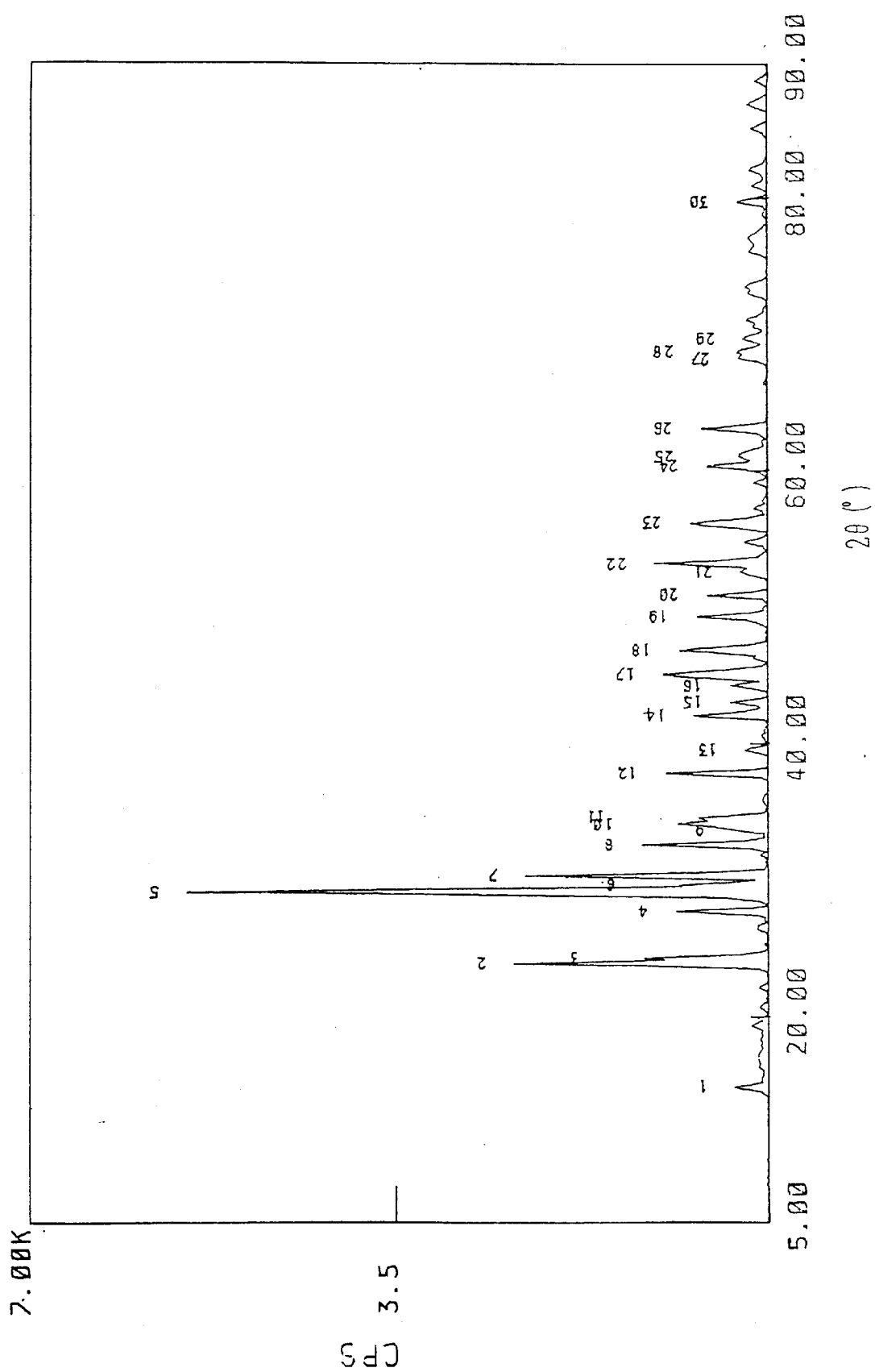

FIG. 8 is an X-ray diffraction chart of $BaPbO_3$ (Example 12).

Figure 9:
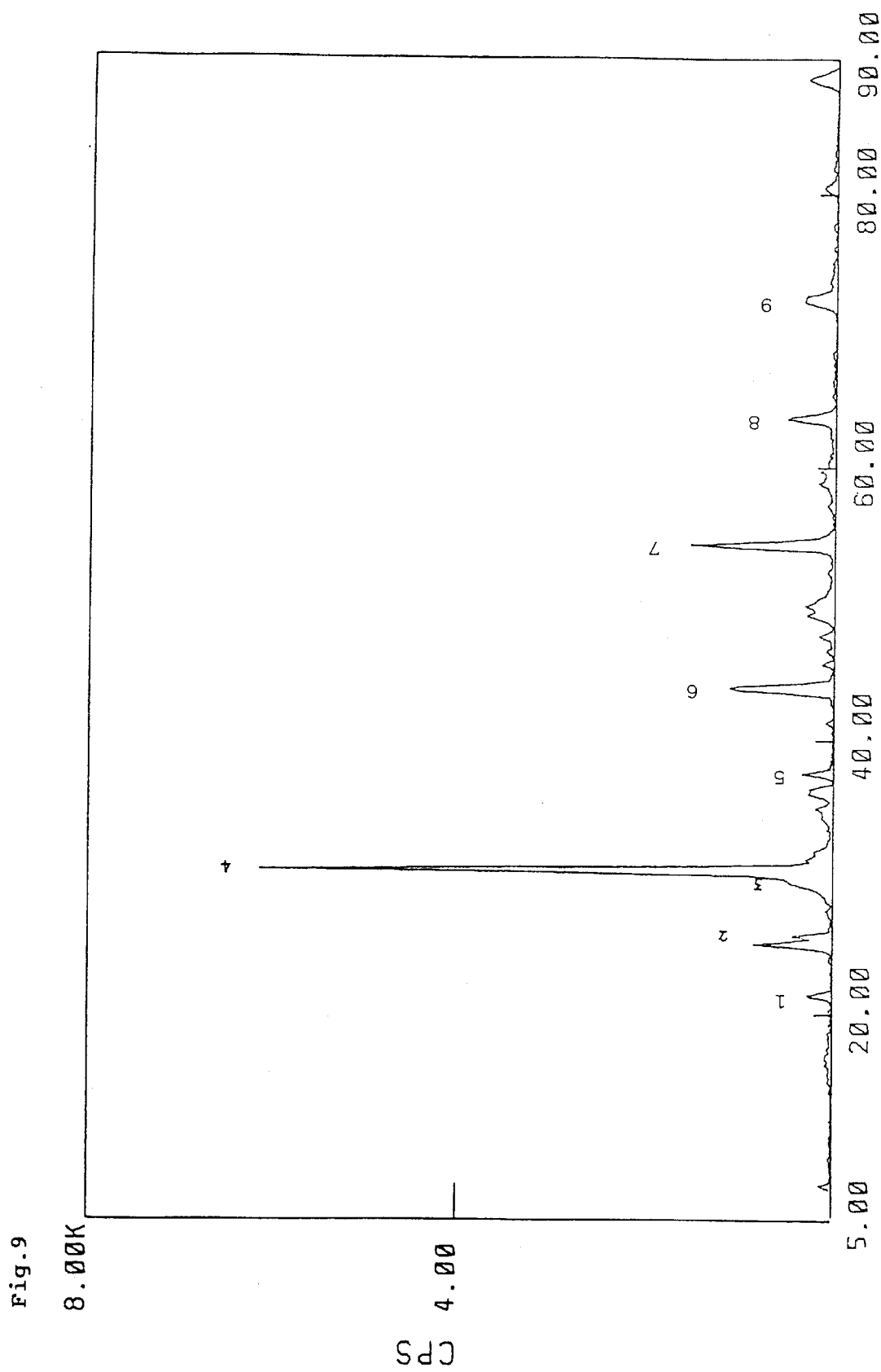

FIG. 9 is an X-ray diffraction chart of $Sr_{0.6}Pb_{0.4}ZrO_3$ (Example 13).

Figure 10:
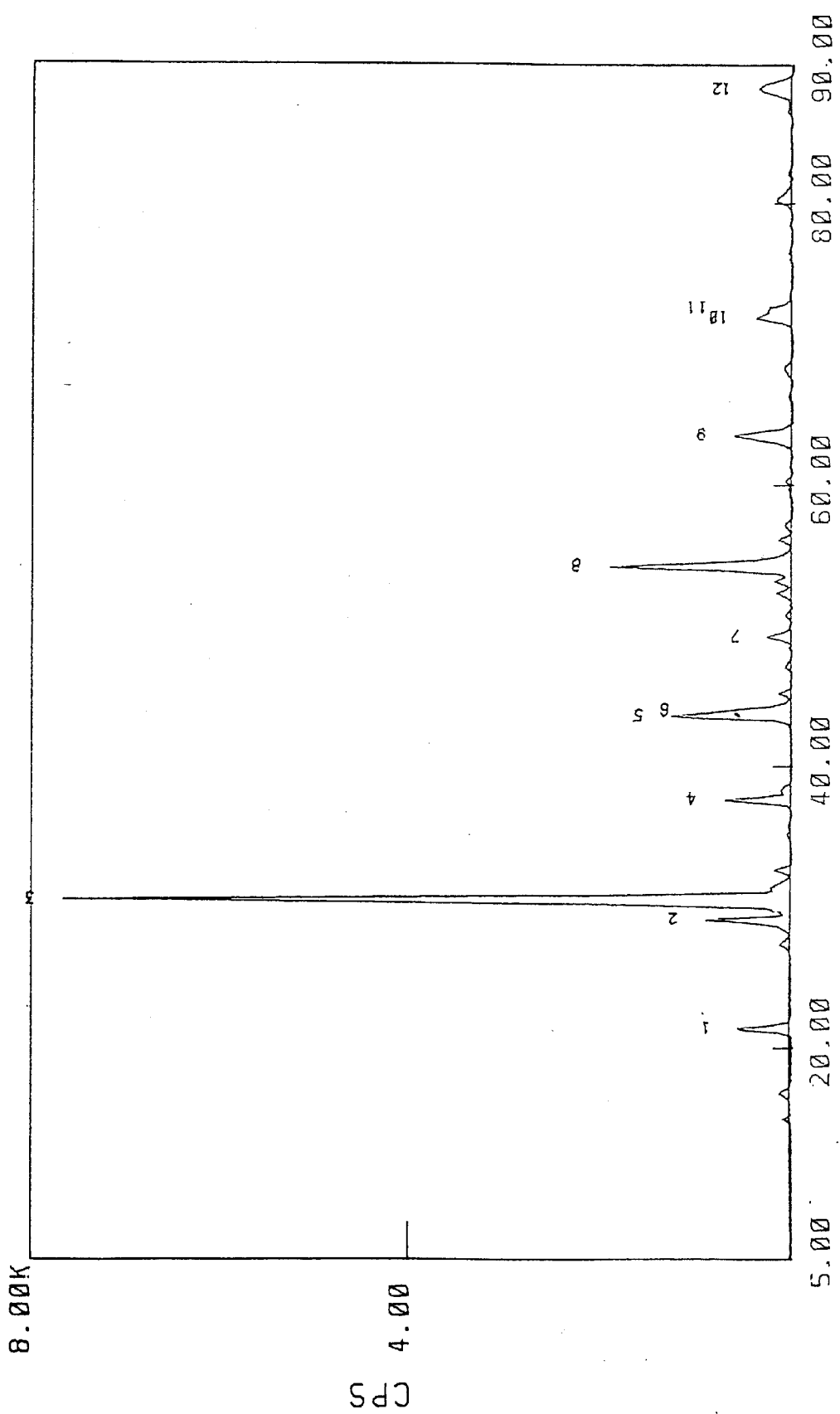

FIG. 10 is an X-ray diffraction chart of $PbZrO_3$ (Example 15).

BEST MODE FOR CARRYING OUT THE INVENTION

Perovskite-type Composite Oxide

The perovskite-type composite oxide, which is used as a support of the present invention, is not a simple mixture nor an amorphous solid solution of metal oxides, but is a solid solution basically having partially or wholly a perovskite-type crystal structure represented by the formula (2):

$$ABO_3 \qquad (2)$$

(wherein, A is a metal ion having a relatively large ionic radius such as a lanthanide metal; B is a metal ion having a relatively small ionic radius). In the formula (2), when A is a divalent metal ion, B is a tetra valent metal ion; when A is a trivalent metal ion, B is a trivalent metal ion. The structure is ideally a cubic system, but it takes a distorted shape of a rhombic system or a monoclinic system depending on the combination of A and B.

In a certain combination of metals, the perovskite-type composite oxide can partially take a composite oxide represented by a K2NiF4 type of the following formula (3), a scheelite type of the following formula (4), a pyrochlore type of the following formula (5) or a garnet type of the following formula (6):

$$A'_2B'O_4 \qquad (3),$$

$$A'B'O_4 \qquad (4),$$

$$A'_2B'_2O_7 \qquad (5),$$

and $$A'_3B'_5O_{12} \qquad (6)$$

(wherein, A' is a metal ion having a large ionic radius and a lower valence such as an alkali metal, an alkaline earth metal or a rare earth metal; B' is a metal ion having a relatively small ionic radius and a higher valence such as a transition metal), and these substances are also treated as a perovskite-type composite oxide in the wide sense. The perovskite-type composite oxide can be identified by analytically comparing with each oxide by means of X-ray diffraction or the like.

It is well known that the perovskite-type composite oxide being different from a simple mixture or an amorphous solid solution of metal oxides, it has functions which are not expressed at all by the original metals, and therefore it is widely studied, for example, as a material having magnetism, piezoelectric effect, pyroelectric property, electro-optical properties or superconductivity. When used as a catalyst, the situation is same, and new properties that are not expressed by simple metal oxides or their mixture are expressed. Further, as a catalyst, the perovskite-type composite oxide often works more efficiently even in a case where it partially has the perovskite-type.

Among perovskite-type composite oxides represented by the above general formula (2), the perovskite-type composite oxide which is especially useful as a catalyst for the synthetic reaction of an aromatic carbonate is the perovskite-type composite oxide whose site B contains a transition metal ion, that is, whose both the sites A and B contain metals taking a trivalent state as oxides, or whose site A contains a metal taking a divalent state as oxide and whose site B contains a metal taking a tetra-valent state as oxide. One of the large special features of perovskite-type composite oxide is that parts or great parts of the A and B ions can be substituted, and thereby the abnormal valence or mixed valences of the B ion are stabilized or oxygen defect can be introduced. By these modifications, an absorbing-desorption property of the compound or a catalytic activity for an oxidation reduction reaction accompanying charge transfer or the like can be increased.

Perovskite-type Composite Oxide of the Above Formula (1)

Group III metals represented by M in the above formula (1) are especially rare earth metals of atomic numbers from 57 to 71 of the group IIIB of the periodic table. Among these rare earth metals, La, Ce, Pr, Nd, Sm, Eu and Gd are preferred, and further La, Ce, Pr, Nd and Sm are especially preferred because they have relatively large ionic radii and thereby can easily form perovskite-type oxides.

Further, in the above formula (1), M' represents a metal having an ionic radius of 0.90 Å or more, more preferably a metal having an ionic radius of 1.0 Å or more. Examples of the metal having an ionic radius of 0.9 Å or more include metals belonging to the groups I to V of the periodic table and having an atomic number of 19 or more, and their specific examples include alkali metals such as K, Rb and Cs, alkaline earth metals such as Ca, Sr and Ba, rare earth metals of Sc and Y, and rare earth metals of atomic numbers from 57 to 71, group m metals such as In and Tl, group IV metals such as Zr, Hf, Sn and Pb, and group V metals such as Bi. Among these metals, K, Ca, Sr, Ba, Y, lanthanide metals of atomic numbers of from 57 to 71, Sn, Pb and Bi are especially preferable.

The metal represented by M' is used in order to substitute a part or great part of a group IIIB metal represented by M, and the ratio is shown by x in the above formula (1). The x takes a number from 0 to 1, but a value preferable to form a perovskite-type structure and exhibit the catalytic activity of the present invention differs every time depending on the combination of the group IIIB metal represented by M and the metal represented by M' (corresponding to the metal at the site A in the formula (2)), and the combination of the metal represented by M and the metal represented by Me (the metal at the site B in the formula (2)). This seems to be attributable to the difference of ionic radii or the difference of possible valences of the metals which are combined. Generally speaking, when the difference between both the ionic radii of the metal represented by M and the substituting metal represented by M' is small, or when the difference between both the possible valences is not large, the substitution is allowed in a relatively wide range. For example, also when both M and M' are rare earth metals, the substitution is allowed in such a manner that x takes a number in the almost whole range from 0 to 1. Further, when M' is Sr, Pb or the like, which has an ionic radius close to that of a lanthanide metal, x can take nearly in the whole range from 0 to 1, and the preferable range of x is relatively large, that is, from 0.05 to 0.9.

On the other hand, the metal represented by M" in the above formula (1) is a transition metal which has a relatively small ionic radius (not more than 0.51 Å), can take plural valences and has redox function, that is, Mn, Cr, Co, Fe, Ni or Cu, preferably Mn, Co or Cu, especially preferably Mn. It is a matter of course that even in this case, a part of the metal can be substituted with a metal of same kind and having a smaller ionic radius. However, to take a perovskite-type structure, since M" corresponds to the site B metal as shown in the above formula (2), the total of the amounts by mole of the metals M and M' corresponding to the site A metal must be equivalent to the amount of the metal M' by mole.

In the above formula (1), y can take, exactly speaking, a number other than 3 because of oxygen deficiency or lattice deficiency of the catalyst, and y takes a number between 2.5 and 3.5, mostly in the range from 2.7 to 3.2.

Perovskite-type Composite Oxide of the Above Formula (1')

Examples of the site A metal represented by L in the above formula (1') include metals having a relatively large ionic radius and taking a divalent state in the form of an oxide, and specifically the examples include alkaline earth metals of the group IIA such as Ca, Sr and Ba, and group IVB metals of Sn and Pb. Among them, Sr, Ba, Sn and Pb, which belong to the groups IIA or IVB, and have an ionic radius of 1.2 Å or more, are especially preferred.

Further, L' of the substituting metal at the site A in the above formula (1) represents metals having an ionic radius of 0.9 Å or more, more preferably metals having an ionic radius of 1.0 Å or more, and more preferably metals having an ionic radius of 1.0 Å or more and taking a monovalent or divalent state. Examples of the metal having an ionic radius of 0.9 Å or more include metals belonging to the groups from I to IV of the periodic table and having an atomic number of 19 or more. The specific examples include alkali metals such as K, Rb and Cs, alkaline earth metals such as Ca, Sr and Ba, rare earth metals such as Sc, Y and rare earth metals of atomic numbers of from 57 to 71, group III metals such as In and Tl, group IV metals such as Sb and Pb, and group V metals such as Bi. Among these metals, K, Ca, Sr, Ba, Y, lanthanide metals of atomic numbers of from 57 to 71, Sn and Pb are preferred.

The metal represented by L' is used in order to substitute a part of the divalent metal represented by L, and the ratio is shown by x in the above formula (1'). The x takes a number of 0 to 1, but a value preferable to form a perovskite-type structure and exhibit the catalytic activity of the present invention differs every time depending on the combination of the divalent metal represented by L and the metal represented by L' (corresponding to the metal at the site A in the formula (2)) and the combination of the metal represented by L and the metal represented by L" (the metal at the site B in the formula (2)). This seems to be attributable to the difference of ionic radii or the difference of possible valences of the metals which are combined. Generally speaking, when the difference between both the ionic radii of the metal represented by L and the substituting metal represented by L' is small, or when the difference between both the possible valences is not large, the substitution is allowed in a relatively wide range. For example, when both L and L' are divalent metals, the substitution is allowed in such a manner that x takes a number in the almost whole range from 0 to 1, and the preferable range of x is relatively large, that is, from 0.05 to 0.9.

On the other hand, the metal represented by L" in the formula (1') mainly takes a tetravalent state in the form of an oxide, but it can take plural valences and has a relatively small ionic radius (not more than 0.80 Å). Examples of such metal include group IVA metals such as Ti and Zr, group IVB metals such as Sn and Pb, and lanthanides of the group IIIA metals such as Ce, Pr and Yb which can take a tetravalent state in the form of an oxide. It is a matter of course that even in this case, a part of the metal can be substituted with a similar metal, taking a tri- or more valent state and having a relatively small ionic radius. However, to take a perovskite-type structure, L" corresponding to the site B metal as shown in the above formula (2), the total of the amounts by mole of the metals L and L' corresponding to the site A metal must be equivalent to the amount of L" metal by mole.

In the above formula (1'), y can take, exactly speaking, a number other than 3 because of oxygen deficiency or lattice deficiency of the catalyst, and y takes a number between 2.5 and 3.5, mostly in the range from 2.7 and 3.2.

Preparation of Perovskite-type Composite Oxide

In the present invention, a catalyst carrying palladium metal or its compound on a perovskite-type composite oxide represented by the above formula (1) or (1') is used. Regarding the perovskite-type oxide, the structure and chemical reactivities including the catalytic activity of the oxide itself have been reported (Reference literature: Advances in Catalysis, vol. 36, 237–328 (1989)).

The perovskite-type composite oxide of the above formula (1) can be prepared, for example, according to the below-mentioned methods. The final product is produced by baking an oxide having the composition ratio of metals represented by the formula (1) at a relatively high temperature; however, the precursor to be baked can be produced by several methods, and the baking conditions needed to produce the perovskite differs depending on the state of the obtained precursor. Generally speaking, the more homogeneously dispersed in terms of oxides the precursor's composition is, the lower the baking temperature at which the perovskite can be produced is, and at the same time the larger the specific area of the product tends to be. The forming of the perovskite-type composite oxide can be identified by analytically comparing with each oxide by means of an X-ray diffraction or the like.

Examples of a specific method for preparing the perovskite-type composite oxide include following. Firstly, co-precipitation method: a mixed aqueous solution of mineral salts of metals is subjected to a co-precipitation process using an alkali, the obtained precipitate is washed with water and filtered, then it is baked preliminarily at a temperature of 300 to 500° C., and finally the material is baked at a high temperature of 700° C. or higher. This is a method which has been widely used conventionally, but to use this method, the precipitate must be insoluble in water. Secondly, hydroxycarboxylic acid addition method: citric acid or malic acid is added to an aqueous solution of mixed nitric salts of the composing metals, the solvent is removed, and the obtained precursor is subjected to heat decomposition. This method is easy in handling and widely applicable, and further it is known that since the precursor obtained by this method has high homogeneity, the perovskite can be formed by baking at a relatively low temperature (550 to 700° C.), and the obtained sintered body frequently has a high specific area of 10 m²/g or more. Furthermore, there is a method called nitric salt decomposition process (NIT process) in which an aqueous solution of mixed nitric salts of metals is directly evaporated to dryness without adding malic acid or the like, and subsequently the dried matter is baked. There is still another method in which a homogeneous aqueous solution of mixed salts is freeze-dried, and the dried matter is baked to prepare the objective product.

The catalyst of the present invention is obtained by supporting a noble metal such as palladium on the so-obtained perovskite-type composite oxide. The supporting can be carried out by an ordinary method such as a precipitation method or an impregnation method.

The precipitation method comprises suspending the perovskite-type composite oxide in an aqueous solution of a palladium salt, for example, $Na_2PdCl_4$, $K_2PdCl_4$, $(NH_4)_2PdCl_4$, $(NH_4)_2PdCl_6$, $(NBu_4)_2PdCl_4$, $Na_2PdBr_4$, $K_2PdBr_4$, $(NBu_4)_2PdBr_4$ or the like, subsequently adding an alkali aqueous solution to neutralize the solution, and as a result, precipitating the palladium compound on the surface of the perovskite-type composite oxide. The impregnation method comprises impregnating the perovskite-type composite oxide with an aqueous solution or an organic solvent solution of a palladium compound which can be converted into palladium metal or palladium oxide by thermal decomposition, and subsequently thermally decomposing the deposited palladium compound.

Furthermore, the impregnation method comprises impregnating the perovskite oxide with an aqueous solution or an organic solvent solution of a palladium compound which can be converted into palladium metal or palladium oxide by thermal decomposition, and subsequently thermally decomposing the deposited palladium compound. Examples of the soluble palladium compound include tetrachloropalladium ammine complex: $(NH_4)_2PdCl_4$, tetraamminepalladium dichloride: $[Pd(NH_3)_4]Cl_2$, $PdCl_2$ in an acidic aqueous solution of hydrochloric acid, $PdBr_2$ in an acidic aqueous solution of hydrobromic acid, palladium dinitro diamine complex: $[Pd(NO_2)_2(NH_3)_2]$ in an ammoniac aqueous solution, $(NBu_4)_2PdBr_4$ in a halogen-containing solvent such as methylene chloride or other volatile organic solvent, olefin complexes such as π-allylpalladium chloride: $[(C_3H_5)PdCl]_2$ and π-allylpalladium bromide: $[(C_3H_5)PdBr]_2$, nitrile complexes such as bisbenzonitrilepalladium dichloride: $Pd(C_5H_6CN)_2Cl_2$, triphenylphosphine complexes such as $PdCl_2(PPh_3)_2$, $Pd(CO)(PPh_3)_3$ and $Pd(CH_2CH_2)(PPh_3)_2$, and the like.

Further, a process which uses a palladium compound soluble in a reaction system but becoming insoluble and depositing by the reduction during the reaction, and as a result, supports the palladium compound on the surface of a perovskite-type composite oxide as a support is also applicable to the preparation of the catalyst. Examples of the palladium compound usable in this method include organic carboxylic acid salts such as palladium formate, palladium acetate and palladium benzoate, complex salts such as palladium acetylacetonato, and salts soluble in the reaction system such as palladium bromide and palladium iodide. In addition, the palladium to be used is not necessarily pure, but the noble metals containing palladium as a main component are also usable in the same way.

Thus, a palladium compound is made to deposit on the surface of a perovskite-type composite oxide as a support, then ordinarily the solvent is evaporated, and the dried product is heated and baked in air, under vacuum or in an inert gas. The temperature of the heating and baking is between 100 to 700° C., and the length of time for the heating and baking is in a range of about 0.5 hour to 50 hours. This heating and baking makes the catalyst system have a stable structure which is preferred in the present invention, but it is necessary to pay care to operational conditions since the treatment at an extremely high temperature and for an extremely long time sometimes causes sintering and so forth to damage catalytic activity or selectivity. The amount of the use of palladium is in the range from 0.01 to 15%, preferably from 0.05 to 10% by weight in terms of palladium metal based on the perovskite-type composite oxide as a support.

Production of an Aromatic Carbonate by Using the Above Catalyst

In the present invention, the objective aromatic carbonate can be produced by reacting an aromatic hydroxy compound with carbon monoxide and oxygen by using the above catalyst in the presence of a quaternary ammonium or phosphonium salt, in the presence of a redox agent, and in the presence or absence of a base.

The aromatic carbonate obtained in the present invention is represented by the following formula (7).

$$RO\text{—}CO\text{—}OR' \qquad (7)$$

(wherein, R and R' are identical to or different from each other, and are each a substituted or unsubstituted aryl having carbon atoms of 6 to 10, preferably a substituted or unsubstituted phenyl, especially preferably an unsubstituted phenyl).

The aromatic hydroxy compound usable to this reaction is an aromatic monohydroxy compound or an aromatic polyhydroxy compound, and examples of the compound include phenol, substituted phenols such as cresol, xylenol, trimethylphenol, tetramethylphenol, ethylphenol, propylphenol, methoxyphenol, ethoxyphenol, chlorophenol and bromophenol, isomers of these phenols, naphthol, substituted naphthols such as methylnaphthol, chloronaphthol and bromonaphthol, isomers of these naphthols, bisphenols such as bisphenol A, and so forth. Among these compounds, phenol is especially preferred.

The quaternary ammonium salt and the quaternary phosphonium salt used in the present invention are represented by the formulae: $R_1R_2R_3R_4NX$ and $R_1R_2R_3R_4PX$, respectively. In the formulae, $R_1$ to $R_4$ are each an alkyl group having carbon atoms of 1 to 8 or an aryl group having carbon atoms of 6 to 12, and they may be identical to or different from each other; X is an anion, and hydroxyl group, an alkoxy group, a phenoxy group, and halides such as chloride, bromide or iodide are preferred. Among the compounds represented by the above formulae, a tetra-n-butylammonium salt and a tetraphenylphosphonium salt are especially preferred. The amount of the quaternary ammonium salt or the quaternary phosphonium salt to be used in the reaction is preferably in the range from 0.1 to 1000, especially preferably in the range from 1 to 100 in terms of the mole ratio to palladium or a palladium compound.

The reaction for producing the aromatic carbonate of the present invention is carried out in the presence of a redox reagent. There is a case where the components of the perovskite of the support for a palladium compound of a catalyst of the present invention contain a redox metal, but the aromatic carbonate is produced by further adding an appropriate redox agent, if necessary.

Examples of the redox agent include compounds of metals of the groups IIIA, IVA, VA, VIA, IB, IIB, VIB and VIIB, the iron group the group VIII) and the rare earth group (the group IIIB) in the periodic table. The compounds of these metals can be used in various oxidation states, for example, as halides, oxides, hydrides, carbonic acid salts, organo carboxylic acid salts, complex salts such as diketone salt, oxalic acid salts and salicylic acid salts, and further as complexes having carbon monoxide, an olefin, an amine, phosphine or the like as a ligand. Among these metal compounds, which have redox activities, preferable ones are compounds of manganese, cobalt, copper, rare earth metals such as lanthanum and cerium, and especially preferred ones are compounds of metals of manganese, cobalt, copper and cerium. The amounts of these redox agents to be used are not specifically limited, but it is preferably in the range from 0.1 to 1000, especially preferably in the range from 0.1 to 100 in terms of the mole ratio to the palladium compound.

The reaction is carried out in the presence or absence of a base. The presence of the base sometimes improves the speed of the reaction and the durability of the catalyst, and brings the improvement of yield, and therefore the base is optionally used. However, since the base finally reacts with the quaternary salt to make the recycling of palladium impossible in some cases depending on the kind, amount or form of the base to be used, the base is not necessarily used. When the base is used, an alkali metal or an alkaline earth metal is used as hydroxide, carbonate, hydrogencarbonate, organic acid salt such as acetate, alkoxide and phenoxide. Further, an organic tertiary amine or pyridine is also used as another form of a base. Examples of the organic base include triethylamine, tripropylamine, tributylamine, trioctylamine, benzyldimethylamine, pyridine, picoline and bipyridine. When a base is used, the amount to be used is in the range from 0.01 to 500 in terms of the mole ratio to palladium.

The reaction for producing the aromatic carbonate in the present invention is carried out by charging the above-mentioned aromatic hydroxy compound, catalyst and promotor component into a reactor, and heating them under pressure of carbon monoxide and oxygen. It is important to take out the water formed by the reaction to the outside of the reaction system as quickly and efficiently as possible in order to efficiently perform the reaction. For this purpose, a method in which a dehydrating agent such as a molecular sieve is added to the reaction system, and so forth are conventionally used, but a method which continuously takes out the formed water to the outside of the reaction system with excess reaction gas by using a gas flow-type reactor is also effective.

Further, it is preferably effective for safety to keep the ratio of the partial pressure of carbon monoxide to that of oxygen constant and also to keep the total pressure constant. The reaction pressure is 1 to 300 atm, preferably 1 to 150 atm, more preferably 2 to 100 atm in terms of the total pressure. In addition, the partial pressure ratio of carbon monoxide to oxygen is preferably kept constant, and the composition ratio is preferably out of the explosion range from the view point of safety. The partial pressure ratio of carbon monoxide to oxygen differs depending on the total pressure and the ratio of the contained inert gas, but it is commonly selected from the range of (5:1) to (30:1). Thus, the composition ratio of the gasses supplied during the reaction is kept constant, so that the gas composition is kept at the most suitable state for the reaction, and at the same time the reaction can be carried out while the water formed during the reaction is continuously removed.

The reaction temperature is in the range from 30 to 200° C., preferably in the range from 50 to 150° C. The reaction time differs depending on the reaction conditions, but it is commonly from several minutes to several hours.

For the reaction, various kinds of inert solvents can be used as the reaction solvent, but the solvent having a relatively high vapor pressure is gradually lost from the reaction system accompanied by the reaction gasses when the reaction is carried out under the conditions of the above-mentioned gas flow system. Therefore, the aromatic hydroxy compound of a reacting compound is usually used as the reaction solvent, and another solvent is not specifically used in many cases.

The production of an aromatic carbonate by using the catalyst carrying a metal of the platinum group on the perovskite-type composite oxide of the present invention can be carried out in various methods. Besides the above-mentioned gas flow-type method, the reaction can be carried out in a closed-reactor batch process by using a high pressure reactor. Further, when the reaction is carried out in a continuous system, the catalyst is placed in a fluidized bed or in a fixed bed, and the reaction can be carried out in a counter-current or cocurrent system.

Figure 1:
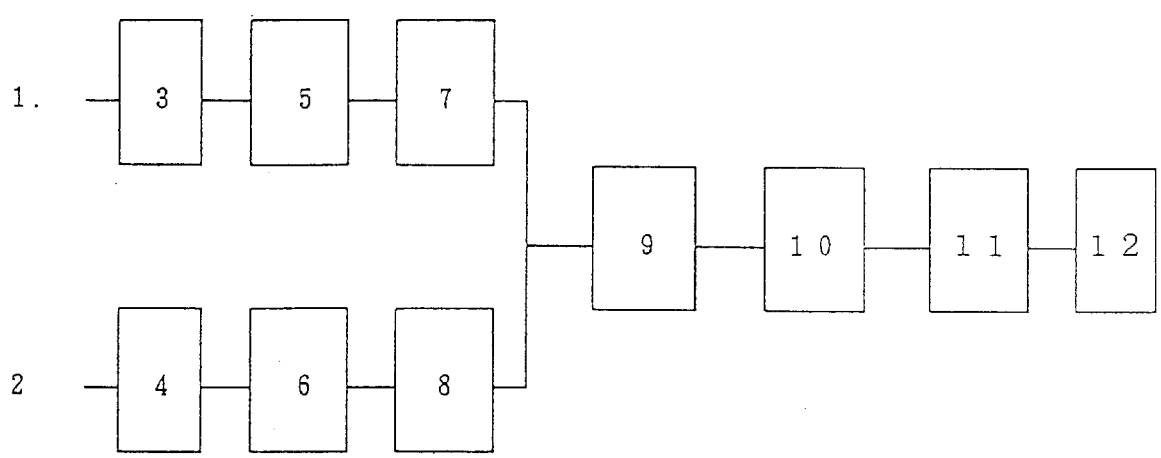
FIG. 1 is a schematic drawing of a small-sized reaction apparatus of a gas-passing type.

FIG. 1 shows the outline of a small-sized gas flow-type reactor as an example.

The reactor shown in FIG. 1 enables the continuous feeding of a mixed gas of carbon monoxide and oxygen (or air), whose molar ratio and partial pressures are both kept constant, at a constant flow rate in the range of about 10 to 800 ml/min. The reactor 10 has a volume of 100 ml, and has the shape of a cylinder of 30 mm in diameter. It is provided with a gas feeding tube and a rotary stirring blade. When the reaction gas 1 is carbon monoxide, and the reaction gas 2 is oxygen (or air), they are each adjusted to a pressure higher than the pressure of the pressure controller 12 which adjusts the specified reaction pressure, by 1 to 5 atm with the pressure controllers 5 and 6 via valves 3 and 4, respectively. According to this system, the gasses each having a specified flow rate are fed through constant flow gas feeding apparatuses (mass flow controller) 7 and 8, and then fed to the reactor 10 through the gas mixing and preheating device 9. The gas components which have passed through the reactor are made to pass through the cold trap 11 and further the pressure controller 12, and then discharged. The pressure of the reactor is adjusted by the pressure controller 12.

In the example of the reactor shown in FIG. 1, the gas which has come out from the reactor is lead to the cold trap 11, parts of the formed water and the solvent are trapped here, and the unreacted gases come outside the system through the pressure controller 12, and they are recovered there. The recovered gasses can be recycled after their gas composition is adjusted if necessary.

After the reaction is completed, the reaction mixture is taken out from the reactor, and the catalyst of the present invention can be separated and recovered by filtration, centrifugal separation, magnetism-applied separation or the like, and recycled. In the case of the fixed bed, the process of the separation is not needed. The objective aromatic carbonate can be separated, purified and isolated by the methods of filtration, distillation, crystallization, etc.

Reactivation of the Catalyst

In the process for producing the aromatic carbonate by using the catalyst of the present invention, the catalyst which has been used in the above-mentioned reaction and whose activity has been lowered can be reactivated by treating it with water and/or a water-miscible organic solvent. Further, the regenerated solid catalyst can be used repeatedly in the above-mentioned reaction. Furthermore, the solid catalyst also can be regenerated in combination with another activating regenerating method, and the so-regenerated catalyst can be used repeatedly in the above-mentioned reaction.

The method for regenerating the solid catalyst in the present invention comprises washing treatments of the solid catalyst having lowered activity with water and/or a water-miscible organic solvent. Each of the two treatments can be carried out by a relatively simple operation, and either method is effective by itself, but the combination of both the methods exhibits larger effect.

The regeneration treatment of the solid catalyst with water is performed by washing the catalyst having lowered activity with water. The catalyst may be once separated from the reaction mixture and taken out from the reaction system, but in the case of the fixed bed, the regeneration can be performed in a state where the catalyst is left filled in the reactor. The treatment is not necessarily carried out only with purified water, but can be carried out with a mixture containing a small amount (10% or less) of a water-miscible organic solvent. Examples of the organic solvent include carbonyl compounds such as acetone, formalin and methyl ethyl ketone, alcohols such as methanol, ethanol, propanol and phenol, cyclic ethers such as tetrahydrofuran, nitrites such as acetonitrile, amides such as N, N dimethylformamide, N, N dimethylacetamide and N-methylpyrrolidone, and polar solvents such as pyridine and dimethyl sulfoxide; however, volatile compounds such as acetone having a boiling point of 150° C. or less, preferably 100° C. or less are preferred because of the little persistence after the cleaning.

Regarding the temperature of the water treatment, there is no special limitation, but the treatment is carried out at a temperature in the range where water can be held in a liquid state, commonly ranging from normal temperature to slightly elevated temperature, that is, in the range of 20 to 100° C. The treatment at higher temperature needs special operations such as pressurization and so forth.

For the regeneration of the catalyst of the present invention, a treatment using a water-miscible organic solvent is preferably carried out together with the treatment using water. The washing treatment using the organic solvent may be carried out before or after the treatment using water, but it is preferable to carry out it before the treatment using water. Naturally, the treatment using water and the treatment using the water-miscible organic solvent can be carried out more than twice alternatively.

As the water-miscible organic solvent used in the present invention, ketones (carbonyl compounds), alcohols, ethers, esters, nitrites, amides, or the like whose mutual solubility with water is 5.0% or more by weight at room temperature are preferred. Examples of such organic solvents include ketones (carbonyl compounds) such as acetone, formalin and methyl ethyl ketone, alcohols such as methanol, ethanol and propanol, phenol, cyclic ethers such as tetrahydrofuran, nitrites such as acetonitrile, amides such as N, N' dimethylacetamide, N, N' dimethylacetamide and N-methylpyrrolidone, and polar solvents which are miscible with water in a wide range such as pyridine and dimethyl sulfoxide. Among them, solvents having a relatively high volatility such as acetone, tetrahydrofuran and acetonitrile are preferred because of little persistence on the catalyst. These organic solvents can be used singly or as a mixture of two or more kinds.

Further, the mutual solubility with water of said organic solvent is about 10% or more. Specifically, the mutual solubility of phenol is about 10% and that of methyl ethyl ketone is about 25% at room temperature, respectively.

The treatment with the water-miscible organic solvent is carried out in almost same operation as the washing treatment with water. That is, the treating temperature is in the range where the organic solvent to be used can be held in a liquid state, commonly ranging from normal temperature to slightly elevated temperature, that is, in the range of 20 to 60° C. The treatment at higher temperature needs special operations such as pressurization and so forth.

EXAMPLES

The present invention will be explained specifically hereafter with examples.

Example 1

Preparation of Perovskite-type Oxide: $La_{0.5}Pb_{0.5}MnO_3$

A solution prepared by dissolving 4.14 g of lead nitrate: $Pb(NO_3)_2$, 5.41 g of lanthanum nitrate hexahydrate: $La(NO_3)_3 \cdot 6H_2O$ and 7.18 g of manganese nitrate hexahydrate: $Mn(NO_3)_2 \cdot 6H_2O$ in a small amount of water was combined with an aqueous solution prepared by dissolving 10.5 g of citric acid in about 50 cc of water to obtain a homogeneous solution, and this solution was heated to evaporate water. The foamed solid obtained by the evaporation to dryness was thermally decomposed, and further baked at 500° C. for 3 hours. The obtained solid powder was again baked at 800° C. for 6 hours in an electric furnace. The X-ray diffraction pattern of the obtained sintered compact had strong peaks at diffraction angles (2θ) of 22.8°, 32.5°, 40.12°, 46.66°, 52.6°, 58.1°, 68.22°, 77.68° and the like as shown in FIG. 2, and thereby it was confirmed that the sintered compact had a perovskite-type structure, and these data agreed with the data in the literature (Journal of the Chemical Society of Japan 1988 (3) p.272–277).

Support of Palladium on a Perovskite-type Oxide: $La_{0.5}Pb_{0.5}MnO_3$

To 50 ml of water was added 148 mg of disodium tetrachloropalladate: $Na_2PdCl4$ to dissolve it, and 5.0 g of the above-obtained perovskite-type oxide was suspended in the solution. This suspension was slowly neutralized with a 5%-caustic soda aqueous solution under stirring to pH=9. After standing for a while, the suspension was filtered, and the matter on the filter was washed with water, the obtained supported catalyst was dried at 110° C. for 16 hours, and it was further baked at 250° C. for 3 hours. Palladium content in the catalyst is about 1.0% by weight in terms of metal based on the perovskite oxide.

Preparation of Diphenyl Carbonate by Using the Above-mentioned Supported Catalyst Into the 100-ml reactor shown in FIG. 1 were charged 50.0 g of phenol, 2000 mg of the above-mentioned catalyst and 986 mg of tetra-n-butylammonium bromide, and the gas inside the reactor was substituted with carbon monoxide. The temperature of the reactor was elevated to 80° C., and at the same time the pressure was increased to 10 bar with carbon monoxide. When the reaction temperature and pressure reached the specified values, the reaction was started and continued for 5 hours under reaction pressure of 10 bar at a reaction temperature of 80° C. by passing carbon monoxide at a flow rate of 500 ml/min (the standard state) and pure oxygen at a flow rate of 25 ml/min (the standard state). After the reaction finished, the reaction mixture in the reactor was taken out, and it was analyzed by gas chromatography with the result that 10.18 g (17.9% yield) of diphenyl carbonate (DPC) was obtained. Byproducts were hardly detected, and the reaction selectivity was 99% or more.

Example 2

Preparation of Perovskite-type Oxide: $Ce_{0.5}Pb_{0.5}MnO_3$

Same as in Example 1, 5.42 g of cerium nitrate hexahydrate: $Ce(NO_3)_3.6H_2O$, 4.14 g of lead nitrate: $Pb(NO_3)_2$ and 7.18 g of manganese nitrate hexahydrate: $Mn(NO_3)_2.6H_2O$ were dissolved in a small amount of water, the obtained solution was combined with an aqueous solution prepared by dissolving 10.5 g of citric acid in about 50 cc of water to obtain a homogeneous solution, and this solution was heated to evaporate water. The foamed solid obtained by the evaporation to dryness was thermally decomposed, and further baked at 500° C. for 3 hours. The obtained solid powder was again baked at 800° C. over night in an electric furnace. It can be identified with the X-ray diffraction chart (Cu—K α ray) of the powder shown in FIG. 3 that the obtained sintered compact has a perovskite-type structure.

Support of Palladium on a Perovskite-type Oxide: $Ce_{0.5}Pb_{0.5}MnO_3$

To 30 ml of water was added 294 mg of disodium tetrachloropalladate: $Na_2PdCl_4$ to dissolve it, and 5.0 g of the above-obtained perovskite-type oxide was suspended in the solution. This suspension was slowly neutralized with a 5%-caustic soda aqueous solution under stirring to pH=9. After standing for a while, the suspension was filtered, and the matter on the filter was washed with water, the obtained supported catalyst was dried at 110° C. over night, and it was further baked at 250° C. for 3 hours. Palladium content in the catalyst was about 2.0% by weight in terms of metal based on the perovskite oxide.

Preparation of Diphenyl Carbonate by Using the Above-mentioned Supported Catalyst Into the same reactor as in Example 1 are charged 50.0 g of phenol, 2000 mg of the above-mentioned catalyst, 1000 mg of tetra-n-butylammonium bromide and 80 mg of manganese acetylacetonato dihydrate: $Mn(acac)_2.2H_2O$, and the gas inside the reactor was substituted with carbon monoxide. The temperature of the reactor was elevated to 80° C., and at the same time the pressure was increased to 10 bar with carbon monoxide. When the reaction temperature and pressure reached the specified values, the reaction was conducted under reaction pressure of 10 bar at a reaction temperature of 80° C. for 3 hours by passing carbon monoxide at a flow rate of 500 ml/min (the standard state) and pure oxygen at a flow rate of 25 ml/min (the standard state). After the reaction finished, the reaction mixture in the reactor was taken out, and it was analyzed by gas chromatography with the result that 8.33 g (14.6% yield) of diphenyl carbonate (DPC) was obtained. Byproducts were hardly detected, and the reaction selectivity was 99% or more.

Example 3

Preparation of Perovskite-type Oxide: $Sr_{0.6}Pb_{0.4}CeO_3$

A solution prepared by dissolving 6.34 g of strontium nitrate: $Sr(NO_3)_2$, 21.7 g of cerium nitrate hexahydrate: $Ce(NO_3)_3.6H_2O$ and 6.62 g of lead nitrate: $Pb(NO_3)_2$ in a small amount of water was combined with an aqueous solution of 21.0 g of citric acid to obtain a homogeneous solution, and this solution was heated to evaporate water. The foamed solid obtained by the evaporation to dryness was thermally decomposed, and further baked at 550° C. for 3 hours. The obtained solid powder was again baked at 750° C. for 4 hours in an electric furnace. The X-ray diffraction pattern of the obtained sintered compact shown in FIG. 4 confirms that the sintered compact has a perovskite-type structure.

Support of Palladium on a Perovskite-type Oxide: $Sr_{0.6}Pb_{0.4}CeO_3$

To 50 ml of water was added 276 mg of disodium tetrachloropalladate: $Na_2PdCl_4$ to dissolve it, and 5.0 g of the above-obtained perovskite-type oxide was suspended in the solution. This suspension was slowly neutralized with a 5%-caustic soda aqueous solution under stirring to pH=9. After standing for a while, the suspension was filtered, and the matter on the filter was washed with water, the obtained supported catalyst was dried at 110° C. for 16 hours, and it was further baked at 250° C. for 3 hours. Palladium content in the catalyst was about 2.0% by weight in terms of metal based on the perovskite oxide.

Preparation of Diphenyl Carbonate by Using the Above-mentioned Supported Catalyst Into the 100-ml reactor shown in FIG. 1 were charged 50.0 g of phenol, 1000 mg of the above-mentioned catalyst, 986 mg of tetra-n-butylammonium bromide and 40 mg of manganese acetylacetonato dihydrate, and the gas inside the reactor was substituted with carbon monoxide. The temperature of the reactor was elevated to 80° C., and at the same time the pressure was increased to 10 bar with carbon monoxide. When the reaction temperature pressure reached the specified values, the reaction was started and continued under reaction pressure of 10 bar at a reaction temperature of 80° C. for 2 hours by passing carbon monoxide at a flow rate of 500 ml/min (the standard state) and pure oxygen at a flow rate of 25 ml/min (the standard state). After the reaction finished, the reaction mixture in the reactor was taken out, and it was analyzed by gas chromatography with the result that 8.85 g (15.5% yield) of diphenyl carbonate (DPC) was obtained. Byproducts were hardly detected, and the reaction selectivity was 99% or more.

Example 4

Preparation of Perovskite-type Oxide: $La_{0.8}Sr_{0.2}MnO_3$

A solution prepared by dissolving 8.66 g of lanthanum nitrate hexahydrate: $La(NO_3)_3.6H_2O$, 1.06 g of strontium nitrate: $Sr(NO_3)_2$ and 7.18 g of manganese nitrate hexahydrate: $Mn(NO_3)_2 \cdot 6H_2O$ in a small amount of water was combined with an aqueous solution prepared by dissolving 10.5 g of citric acid in about 50 cc of water to obtain a homogeneous solution, and this solution was held at about 70° C. under reduced pressure to evaporate water. The foamed solid obtained by the evaporation to dryness was thermally decomposed, and further baked at 500° C. for 3 hours. The obtained solid powder was again baked at 900° C. for 4 hours in an electric furnace. The X-ray diffraction pattern of the obtained sintered compact shown in FIG. 5 confirms that the sintered compact has a perovskite-type structure.

Support of Palladium on a Perovskite-type Oxide: $La_{0.8}Sr_{0.2}MnO_3$

To 50 ml of water was added 296 mg of disodium tetrachloropalladate: $Na_2PdCl_4$ to dissolve it, and 5.0 g of the above-obtained perovskite-type oxide was suspended in the solution. This suspension was slowly neutralized with a 5%-caustic soda aqueous solution under stirring to pH=9. After standing for a while, the suspension was filtered, and the matter on the filter was washed with water, the obtained supported catalyst was dried at 110° C. over night, and it was further baked at 250° C. for 3 hours. Palladium content in the catalyst was about 2.0% by weight in terms of metal based on the perovskite oxide.

Preparation of Diphenyl Carbonate by Using the Above-mentioned Supported Catalyst Into the 100-ml reactor shown in FIG. 1 were charged 50.0 of phenol, 1000 mg of the above-mentioned catalyst, 1000 mg of tetra-n-butylammonium bromide and 220 mg of sodium phenolate, and the gas inside the reactor was substituted with carbon monoxide. The temperature of the reactor was elevated to 80° C., and at the same time the pressure was increased to 10 bar with carbon monoxide. When the reaction temperature and pressure reached the specified values, the reaction was started and continued under reaction pressure of 10 bar at a reaction temperature of 80° C. for 3 hours by passing carbon monoxide at a flow rate of 500 ml/min (the standard state) and pure oxygen at a flow rate of 25 ml/min (the standard state). After the reaction finished, the reaction mixture in the reactor was taken out, and it was analyzed by gas chromatography with the result that 7.65 g (13.4% yield) of diphenyl carbonate (DPC) was detected. Byproducts were hardly detected, and the reaction selectivity was 99% or more.

Examples 5 Through 15

Almost in the same way as in Example 1, various kinds of perovskite-type oxides were prepared by using the nitrate salt of each metal and citric acid, and diphenyl carbonate was prepared by using a catalyst carrying palladium in an amount of 1 to 2.5% by weight in terms of metal as shown in Table 1, with the same equipment and under the same conditions as in Example 1 as follows: 50.0 g of phenol, 968 mg of tetrabutylammonium bromide and 80 mg of manganese acetylacetonato dihydrate were charged; the reaction was carried out at a reaction temperature of 80° C., under a reaction pressure of 10 bar, at a flow rate of carbon monoxide of 500 ml/min, at a flow rate of oxygen of 25 ml/min and for a reaction time of 2 hours. The results are shown in Table 1. The presence or absence of the manganese salt in the reaction is also shown in the table.

TABLE 1

|  | Catalyst composition | Amount of catalyst | DPC yield (rate %) | DPC selectivity % | Mn salt presence |
| --- | --- | --- | --- | --- | --- |
| Example 5 | 2% $Pd/Ce_{0.6}Pb_{0.4}MnO_3$ | 1000 mg | 8.53 g (15.0%) | >99 | present |
| Example 6 | 2% $Pd/Ce_{0.6}Pb_{0.4}CoO_3$ | 1000 mg | 8.53 g (14.7%) | >99 | present |
| Example 7 | 2% $Pd/La_{0.6}Pb_{0.4}CuO_3$ | 1000 mg | 9.03 g (15.9%) | >99 | present |
| Example 8 | 2.0% $Pd/La_{0.6}Pb_{0.4}MnO_3$ | 1000 mg | 8.07 g (14.2%) | >99 | absent |
| Example 9 | 2.0% $Pd/La_{0.5}Pb_{0.5}MnO_3$ | 1000 mg | 8.57 g (15.0%) | >99 | absent |
| Example 10 | 2.0% $Pd/Nd_{0.6}Pb_{0.4}MnO_3$ | 1000 mg | 8.11 g (14.2%) | >99 | absent |
| Example 11 | 2.5% $Pd/Ba_{0.6}Pb_{0.4}ZrO_3$ | 1000 mg | 8.40 g (14.8%) | >99 | present |
| Example 12 | 2% $Pd/BaPbO_3$ | 1000 mg | 8.40 g (14.8%) | ~99 | present |
| Example 13 | 2% $Pd/Sr_{0.6}Pb_{0.4}ZrO_3$ | 1000 mg | 8.80 g (15.5%) | >99 | present |
| Example 14 | 2.0% $Pd/Pr_{0.6}Pb_{0.4}MnO_3$ | 1000 mg | 7.83 g (13.8%) | >99 | absent |
| Example 15 | 2% $Pd/PbZrO_3$ | 1000 mg | 9.52 g (16.7%) | >99 | present |

Further, FIGS. 6 to 10 show the X-ray diffraction charts of some perovskite-type oxides.

Examples 16

Preparation of Perovskite-type Oxide $PbZrO_3$

Into 100 ml of isopropanol were added 9.5 g of lead acetate trihydrate: $Pb(OCOCH_3)_2 \cdot 3H_2O$ and 10.5 g of citric acid, and the mixture was heated to dissolve them. To the obtained solution was added 9.8 g of zirconium tetra-n-butoxide $Zr(n-C_4H_9O)_4$ at once, and they were mixed well and heated to evaporate the solvent. The remaining solid was heated at 300° C. or higher to decompose it, the decomposition product was pulverized in a mortar, and the obtained powder was sintered at 650° C. for 6 hours to obtain a perovskite-type composite oxide $PbZrO_3$. The XRD analysis chart of the oxide showed the same pattern as that obtained in Example 15.

Support of Palladium on $PbZrO_3$ and Preparation of Diphenyl Carbonate

In the same manner as in Example 2, a 2% Pd-supported catalyst was prepared, and diphenyl carbonate was prepared by using 1000 mg of the prepared catalyst in the same manner as in Example 1, with the same apparatus and under same conditions as in Example 1 as follows: 50.0 g of is phenol, 968 mg of tetrabutylammonium bromide and 80 mg of manganese acetylacetonato dihydrate were charged; the reaction was carried out at a reaction temperature of 80° C., under a reaction pressure of 10 bar, at a flow rate of carbon monoxide of 500 ml/min, at a flow rate of oxygen of 25 ml/min, and for a reaction time of 2.5 hours or 5 hours, separately.

Resultingly, the yield of DPC was 9.82 g (17.2% yield) by 2.5-hour reaction, and 11.7 g (21.0% yield) by 5-hour reaction, respectively. In either reaction, byproducts was hardly detected, and the reaction selectivity was 99% or more.

Reactivation of Catalyst

Recovery of Solid Catalyst

The above reaction mixture was taken out from the reactor together with the catalyst, the catalyst was separated by filtration, the catalyst on the filter paper was sufficiently washed with ethyl acetate, and the catalyst was dried. The weight of the obtained solid catalyst was 1022 mg.

Reaction by Using the above Recovered Catalyst

The reaction was carried out for 3 hr by adding a new raw material and promotor in the presence of the whole of the recovered catalyst in the same apparatus under the same conditions as in the above reaction, and as a result, the amount of DPC obtained was 4.20 g (7.4% yield).

Regeneration of Catalyst

The catalyst used in the above repeated reaction was again filtered and recovered, the catalyst as-held on the filtration apparatus was washed with about 30 ml of acetone under suction filtration. Subsequently, it was washed with about 15 ml of water, and dried. The amount of the catalyst was 975 mg, there being some process loss.

Preparation of Aromatic Carbonate with the Regenerated Catalyst

The reaction was carried out for 3 hr in the presence of the whole of the regenerated catalyst in the same apparatus under the same conditions as in the above-mentioned reaction, and as a result, it turned out that 7.40 g (13.0% yield) of DPC had been obtained, and the original activity of the solid catalyst was almost regenerated.

Comparative Examples 1 through 3

By using commercial titanium oxide (anatase) $TiO_2$, $CeO_2$ or $Bi_2O_3$, a 2.0 wt. % palladium-supported catalyst was prepared, respectively in the same manner as in Example 1. Diphenyl carbonate was prepared by using these catalysts with the same apparatus and under same conditions as in Examples as follows: 50.0 g of phenol, 968 mg of tetrabutylammonium bromide and 80 mg of manganese acetylacetonato dihydrate were charged; the reaction was carried out at a reaction temperature of 80° C., under a reaction pressure of 10 bar, at a flow rate of carbon monoxide of 500 ml/min, at a flow rate of oxygen of 25 ml/min, and for a reaction time of 2 hours. The results are shown in Table 2.

Comparative Examples 4 and 5

To an aqueous solution of cerium nitrate hexahydrate $Ce(NO_3)_3.6H_2O$ was added equimolar citric acid, the obtained solution was slowly evaporated to dryness followed by heat decomposition, and further the decomposed product was baked at 550° C. for 12 hr. On the obtained cerium oxide powder, 2% by weight of palladium was supported to prepare a supported catalyst in the same manner as in Example 2.

In Comparative Example 4, into the same apparatus as in Example 1 and followed examples were charged 50.0 g of phenol, 1000 mg of the above-obtained catalyst, 1000 mg of tetra-n-butylammonium bromide and 80 mg of manganese acetylacetonate dihydrate, and they were made to react at a reaction temperature of 80° C., under a reaction pressure of 10 bar, at a flow rate of carbon monoxide of 500 ml/min, at a flow rate of oxygen of 25 ml/min and for 2 hr. Further, Comparative Example 5 was carried out under the same conditions as in Comparative Example 4 except that 22 mg of sodium phenolate was further added to the reaction conditions of Comparative Example 4. The results are shown in the following Table 2.

Comparative Examples 6 and 7

Preparation of Manganese Oxide Powder

To a solution prepared by dissolving 126 g (1 mol) of manganese (II) chloride in 500 ml of water was added dropwise a solution of 85 g (2.125 mol) sodium hydroxide dissolved in 200 ml of water. So-obtained precipitate was filtered under reduced pressure, washed with water and dried. Subsequently, this was treated by heating at 300° C. for 3 hr and at 500° C. for 2 hr.

Support of Palladium on Manganese Oxide Powder

At room temperature, to the slurry containing 58.5 g of the above-obtained manganese oxide powder in 300 ml of water was added 60 ml of a solution whose palladium content in water was 15% and which contained 10 g of sodium tetrachloropalladate (II), and subsequently the above slurry was made alkaline with a 5% sodium hydroxide aqueous solution. The suspended solid was separated by suction filtration and dried at 100° C. The content of Pd, which was carried on the support consisting of the manganese oxide powder, in the catalyst was about 2.5% by weight in terms of metal.

Preparation of Diphenyl Carbonate Using the Above-mentioned Supported Catalyst Using the same 100-ml reactor as in Examples 1 to 14, the reaction was carried out in the presence of 1000 mg of the above-mentioned supported catalyst (2.5% Pd/Manganese oxide) under the same conditions as in the examples, that is, in each case of the addition (Comparative Example 6) or no addition (Comparative Example 7) of disodium phenoxide, 50.0 g of phenol and 1000 mg of tetra-n-butylammonium bromide were charged, and the reaction was carried out at a reaction temperature of 80° C., under a reaction pressure of 10 bar, at a flow rate of carbon monoxide of 500 ml/min, at a flow rate of oxygen of 25 ml/min and for a reaction time of 2 hours. The obtained results are shown in the following Table 2 together with other comparative examples.

Comparative Example 8

Reaction was carried out by using 50.0 g of phenol, 2000 mg of a commercial 1%-Pd on carbon (PD-KAB-02 supplied by N. E. CHEMCAT Corporation), 80 mg of manganese (II) acetylacetonate dihydrate: $Mn(acac)_2 \cdot 2H_2O$, 968 mg of tetra-n-butylammonium bromide and 220 mg of sodium phenolate under the same conditions as in the Examples for 2 hours. The results are shown in the following Table 2.

TABLE 2

| | Catalyst composition | Amount of catalyst | DPC yield (rate %) | DPC selectivity % | Base presence | Mn salt presence |
|---|---|---|---|---|---|---|
| Comparative Example 1 | 2% Pd/TiO$_2$ | 1000 mg | 2.43 g (4.3%) | 94 | absent | present |
| Comparative Example 2 | 2% Pd/CeO$_2$ | 1000 mg | 2.32 g (4.1%) | 86 | absent | present |
| Comparative Example 3 | 2% Pd/Bi$_2$O$_3$ | 1000 mg | 1.98 g (3.5%) | 90 | absent | present |
| Comparative Example 4 | 2% Pd/CeO$_2$ | 1000 mg | 2.23 g (3.9%) | 90 | absent | present |
| Comparative Example 5 | 2% Pd/CeO$_2$ | 1000 mg | 4.20 g (7.4%) | 98 | PhONa 220 mg | present |
| Comparative Example 6 | 2.5% Pd/MnO$_2$ | 1000 mg | 4.76 g (8.4%) | 98 | absent | present |
| Comparative Example 7 | 2.5% Pd/MnO$_2$ | 1000 mg | 5.65 g (9.9%) | 99 | PhONa 220 mg | present |
| Comparative Example 8 | 1% Pd/activated carbon | 2000 mg | 5.91 g (10.4%) | 99 | PhONa 220 mg | present |

Effect of Invention

The present invention can provide supported catalysts having high activity and selectivity enabling the production of an aromatic carbonate in high yield and selectivity, and economically from an aromatic hydroxy compound, carbon monoxide and oxygen, and a method for the reaction using said catalyst.

What is claimed is:

1. A catalyst for the synthetic reaction of an aromatic carbonate in which a palladium compound is supported on the perovskite-type composite oxide represented by the following formula (1):

$$M_{(1-x)}M'_xM''O_y \quad (1)$$

(wherein, M is a group IIIB metal; x is a number of 0.05 to 0.9; M' is a metal selected from the group consisting of K, Ca, Sr, Ba, Y, Sn, Pb, and Bi; M" is Mn, Cr, Co, Fe, Ni or Cu; y is a number of 2.5 to 3.5) and the palladium accounts for 0.01 to 15% of the catalyst by weight.

2. A catalyst described in claim 1 wherein M is a lanthanide from La to Gd in the above-mentioned formula (1).

3. A catalyst described in claim 1, wherein M" is Mn, Co or Cu in the above-mentioned formula (1).

4. A method for preparing an aromatic carbonate characterized in that, in a method for preparing the aromatic carbonate from an aromatic hydroxy compound, carbon monoxide and oxygen in the presence of a quaternary ammonium or phosphonium salt, and a redox reagent, and in the absence of a base, the reaction is carried out by using a catalyst in which a palladium compound is supported on the perovskite-type composite oxide represented by the following formula (1):

$$M_{(1-x)}M'_xM''O_y \quad (1)$$

(wherein M is a group IIIB metal; x is a number of 0 to 1; M' is a metal having an ionic radius of 0.90 Å or more; M" is Mn, Cr, Co, Fe, Ni or Cu; y is a number of 2.5 to 3.5) and the palladium accounts for 0.01 to 15% of the catalyst by weight.

5. A method for preparing an aromatic carbonate described in claim 4 wherein a compound containing a metal ion of cerium, cobalt, copper or manganese is used as the redox agent.

6. A method for preparing an aromatic carbonate comprising reacting an aromatic hydroxy compound with carbon monoxide and oxygen using a catalyst which has been reactivated by treatment with one of the compounds selected from the group consisting of water, a water-miscible organic solvent, a ketone, an alcohol, an ester, a nitrile compound, and an amide, in the presence of a quaternary ammonium or phosphorus salt.

7. The method for preparing an aromatic carbonate described in claim 4 wherein M is a lanthanide from La to Gd.

8. The method for preparing an aromatic carbonate described in claim 4 wherein M' is a metal having an ionic radius of 1.0 Å or more.

9. The method for preparing an aromatic carbonate described in claim 4 wherein M' is a metal selected from the group consisting of K, Ca, Sr, Ba, Y, a lanthanide metal of atomic number of from 57 to 71, Sn, Pb, and Bi.

10. The method for preparing an aromatic carbonate described in claim 4 wherein M" is Mn, Co or Cu.

* * * * *